United States Patent [19]

Cassidy et al.

[11] 4,315,941
[45] Feb. 16, 1982

[54] URAZOLE ANALOGS OF PROSTAGLANDIN DERIVATIVES

[75] Inventors: Frederick Cassidy, Harlow; Richard W. Moore, Bishop Stortford, both of England

[73] Assignee: Beecham Group Limited, England

[21] Appl. No.: 164,158

[22] Filed: Jun. 30, 1980

[30] Foreign Application Priority Data

Jul. 12, 1979 [GB] United Kingdom ............... 24235/79
Jul. 30, 1979 [GB] United Kingdom ............... 26432/79

[51] Int. Cl.³ .................... A61K 31/41; C07D 249/12
[52] U.S. Cl. .................................... 424/269; 548/264
[58] Field of Search ........................ 548/264; 424/269

[56] References Cited

FOREIGN PATENT DOCUMENTS 6718 1/1980 European Pat. Off. ............ 424/269
7180 1/1980 European Pat. Off. ............ 424/269

*Primary Examiner*—Alton D. Rollins
*Attorney, Agent, or Firm*—Jacobs & Jacobs

[57] ABSTRACT

Compounds of the formula (I):

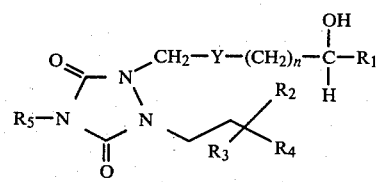

wherein:
n is 3 to 5;
Y is $-CH_2-CH_2$ or $-CH=CH-$ or $-C\equiv C-$
$R_1$ is $C_{1-4}$ alkyl;
$R_2$ is hydrogen, $C_{1-4}$ alkyl or phenyl;
$R_3$ is hydroxy or protected hydroxy;
$R_4$ is hydrogen, $C_{1-9}$ alkyl, $C_{3-8}$ cycloalkyl, phenyl, naphthyl, any of which phenyl moieties or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; and
$R_5$ is $C_{1-6}$ alkyl having useful pharmacological activity, compositions containing them and processes for their preparation.

9 Claims, No Drawings

URAZOLE ANALOGS OF PROSTAGLANDIN DERIVATIVES

This invention relates to novel compounds having pharmacological activity, to a process for their preparation, to intermediates useful in that process and to pharmaceutical compositions containing them.

Offenlegungsschrift No. 2323193 discloses that pyrazolidine derivatives of the formula (I)':

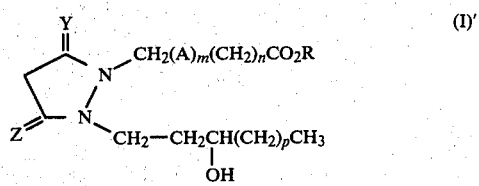

wherein: A is CH=Ch or C≡C; R is H, an alkali metal, an amine salt, or a ≯ 12C hydrocarbon or chlorohydrocarbon residue: m is 0 or 1; n is 0-6; p is 0-6; and Y and Z are O or H except that Y and Z are not both O; have similar biological properties to the prostaglandins or are antagonists of prostaglandins.

French Patent Application No. 2258376 discloses that 10-aza prostaglandins of formula (II)'':

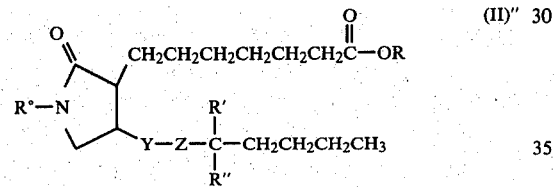

wherein: R=H or lower alkyl; R' and R''=CH$_3$ or C$_2$H$_5$; R°=H or lower alkyl; Y=—CH$_2$—CH$_2$—, or —CH=CH—; Z=—CO or —CH(~OH)—; are useful in the treatment of blood pressure and gastro-intestinal disorders, and in the preparation for confinement.

Belgian Pat. No. 835989 discloses that compounds of the formula (III)'':

$$\begin{array}{c} X \\ (CH_2)_m \diagdown \diagup CH_2-Y-(CH_2)_n-R_1 \\ \diagup \diagdown \\ Z-N \diagdown R_2 \\ \diagdown R_4 \\ R_3 \end{array} \quad (III)''$$

wherein: X is CO, protected CO, CROH in which R is hydrogen or C$_{1-4}$ alkyl and in which the OH moiety may be protected; Y is CH$_2$CH$_2$ or CH=CH; Z is CO or CH$_2$; n is 1 to 8; m is 1, 2 or 3; R$_1$ is hydrogen, CH$_2$OH, CH$_2$OH in which the OH moiety is protected, CO$_2$W wherein W is hydrogen or CO$_2$W represents an ester group in which the ester moiety contains from 1 to 12 carbon atoms, or CONH$_2$; R$_2$ is hydrogen, C$_{1-4}$ alkyl, or taken together with R$_3$ and the carbon atom to which it is attached represents a carbonyl group; R$_3$ is hydrogen, hydroxy or protected hydroxy; R$_4$ is hydrogen or C$_{1-9}$ alkyl; and salts thereof; have useful pharmacological activity.

A novel class of compounds also having useful pharmacological activity has now been discovered, which compounds are structurally distinct from the prior art referred to above.

Accordingly the present invention provides a compound of the formula (I):

$$\begin{array}{c} OH \\ | \\ O=\diagup \diagdown N-CH_2-Y-(CH_2)_n-C-R_1 \\ | \\ R_5-N \diagdown N \diagup R_2 \quad H \\ \| \diagdown \diagup \\ O \quad R_3 \quad R_4 \end{array} \quad (I)$$

wherein:
n is 3 to 5;
Y is —CH$_2$—CH$_2$ or —CH=CH— or —C≡C—
R$_1$ is C$_{1-4}$ alkyl;
R$_2$ is hydrogen, C$_{1-4}$ alkyl or phenyl;
R$_3$ is hydroxy or protected hydroxy;
R$_4$ is hydrogen, C$_{1-9}$ alkyl, C$_{3-8}$ cycloalkyl, phenyl, naphthyl, any of which phenyl moieties or naphthyl moieties may be substituted by one or more halogen, trifluoromethyl, C$_{1-6}$ alkyl, hydroxy, C$_{1-6}$ alkoxy, phenyl C$_{1-6}$ alkoxy or nitro groups; and
R$_5$ is C$_{1-6}$ alkyl.
Preferably n is 4 or 5.
Suitable values for Y include —CH$_2$—CH$_2$ or cis —CH=CH—.
A preferred value for Y is cis —CH=CH—.
Suitable examples of R$_1$ include methyl, ethyl, n- and iso propyl, and n-, sec- and tert-butyl.
Suitable examples of R$_2$ include hydrogen, methyl, ethyl, and phenyl. Preferred examples of R$_2$ include methyl.
Suitable protected hydroxy groups R$_3$ include readily hydrolysable derivatives such acylated hydroxy groups in which the acyl moiety contains 1 to 4 carbon atoms, for example the acetoxy group; and hydroxy groups etherified by inert groups such as benzyl or methyl. Preferably however R$_3$ is hydroxy.
Suitable groups R$_4$ when R$_4$ is an alkyl group include C$_{4-9}$ alkyl groups. Such C$_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, R$_4$ may be a group CH$_2$R$_6$, CH(CH$_3$) R$_6$ and C(CH$_3$)$_2$R$_6$ wherein R$_6$ is a straight chain alkyl group such that the carbon content of the resultant group R$_4$ is 4 to 9.
In general preferred groups R$_4$ when R$_4$ is an alkyl group include straight chain pentyl, hexyl and heptyl groups. Other preferred groups R$_4$ include groups CH(CH$_3$)R$_6$ C(CH$_3$)$_2$R$_6$ wherein R$_6$ is straight chain butyl, pentyl and hexyl.
When R$_4$ is a C$_{3-8}$ cycloalkyl moiety, the moiety may suitably be a C$_{5-8}$ cycloalkyl moiety such as a cyclohexyl moiety. It may also be a cyclopropyl moiety.
When R$_4$ is an aryl group as previously defined, suitable groups R$_4$ include phenyl and naphthyl which groups may be substituted by normally one, two or three groups selected from those substituent groups listed hereinbefore. Examples of suitable substituent groups include fluorine, chlorine and bromine atoms and CF$_3$, methyl, ethyl, n- and iso-propyl, methoxy, ethoxy, n- and iso-propoxy and nitro groups. Other examples of such groups include hydroxy and benzyloxy. Preferably the aryl moieties when substituted by such groups will be mono- or disubstituted.

Suitable examples of $R_5$ include methyl, ethyl, n- and iso-propyl and n-butyl and such groups branched in the alkyl moiety by one or two methyl groups (at the same or different carbon atoms). Preferred $R_5$ groups include methyl.

One particularly suitable sub-group of compounds within formula (I) is of formula (II):

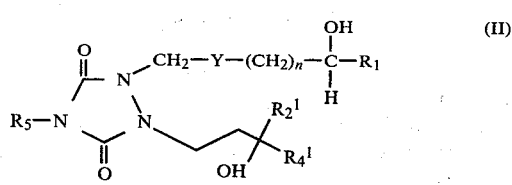

wherein:
Y, n, $R_1$ and $R_5$ are as defined in formula (I);
$R^1_2$ is hydrogen, methyl, ethyl or phenyl; and $R^1_4$ is hydrogen or $C_{1-9}$ alkyl Preferably n is 4 or 5.

Suitably Y is $-CH_2CH_2-$ or cis $-CH=CH-$.

A preferred value for Y is cis $-CH=CH-$.

Suitable $R_1$ are as listed as suitable under formula (I).

Suitable $R^1_2$ may be hydrogen, methyl or ethyl.

While $R^1_4$ may be hydrogen or a $C_{1-9}$ alkyl group in formula (II), it is normally a $C_{4-9}$ alkyl group. In such cases suitable and preferred straight chain and branched groups $R^1_4$ include those previously described as suitable and preferred for the group $R_4$ when $R_4$ is a $C_{4-9}$ alkyl group. Such preferred groups $R^1_4$ include straight chain pentyl, hexyl and heptyl. Other preferred groups $R^1_4$ include $CH(CH_3)R^1_6$ and $C(CH_3)_2R^1_6$ wherein $R^1_6$ is straight chain butyl, pentyl or hexyl.

Preferably $R_5$ is methyl or ethyl, in particular methyl.

From the aforesaid it will be realised that one preferred group within formula (II) is of formula (III):

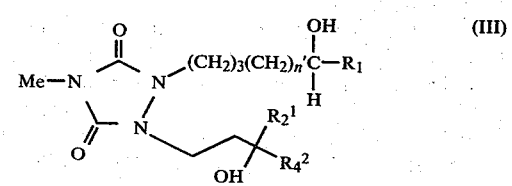

wherein:
n' is 4 or 5
$R_1$ is as defined in formula (I);
$R^1_2$ is hydrogen, methyl or ethyl; and
$R^2_4$ is a $C_{4-9}$ alkyl group.

Suitable $R_1$ are as listed as suitable under formula (I). Suitable and preferred groups $R^2_4$ include those listed hereinbefore for $R^1_4$ when $R^1_4$ is a $C_{4-9}$ alkyl group.

Another preferred group within formula (II) is of formula (IV):

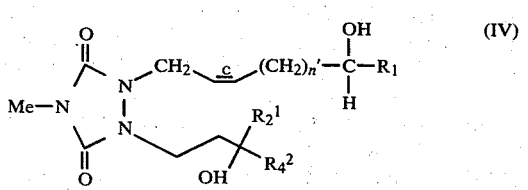

wherein the variables are as defined in formula (III). Suitable and preferred values of $R_1$ and $R^1_4$ are as hereinbefore described for compounds of formula (III).

Another suitable sub-group of compounds within formula (I) is of formula (V):

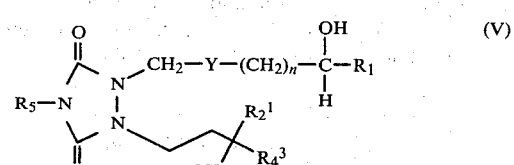

wherein:
Y, n, $R_1$, and $R_5$ are as defined in formula (I);
$R^1_2$ is hydrogen, methyl, ethyl or phenyl; and
$R^3_4$ is a group of formula (VI):

wherein: V, W and Z are each hydrogen or fluorine, chlorine or bromine atoms, or $CF_3$, methyl, ethyl, n- or iso-propyl, methoxy, ethoxy, n or iso-propoxy or nitro groups.

In formula (V) it is preferred that n is 4

Suitable $R_1$ are as listed as suitable under formula (I).

In formula (VI) V and W will often be hydrogen.

Often in formula (V) $R_5$ will be methyl or ethyl, preferably methyl.

A further sub-group of compounds within the formula (I) is of formula (VII):

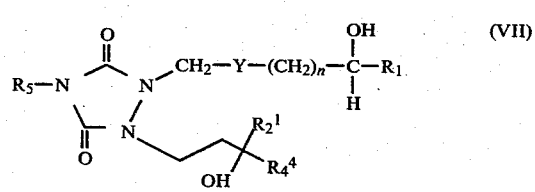

wherein the variable groups are as defined in formula (II) and $R^4_4$ is a group of formula (VIII):

wherein r is 0-3, more suitably 1.

Suitable and preferred variable groups except for $R^4_4$ in formula (VII) are as in formula (II).

A group of compounds within the formula (VIII) is of formula (IX):

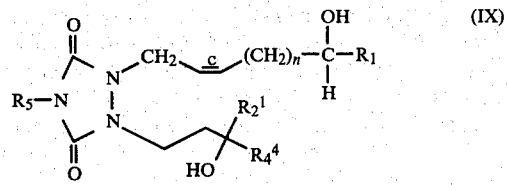
(IX)

wherein the variable groups are as defined in formula (VIII). Suitable and preferred values of $R_1$, $R^1_2$ and $R_5$ are as so described under formula (II).

Process Variant (a)

The invention also provides a process for the preparation of a compound of the formula (I), which process comprises reacting a compound of formula (X):

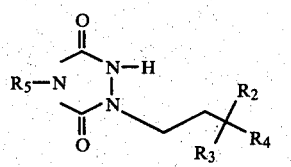
(X)

wherein $R_2$, $R_3$, $R_4$, and $R_5$ are as defined in formula (I) with a compound of formula (XI):

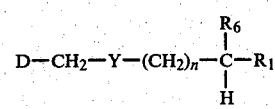
(XI)

wherein D is a group readily displaced by nucleophiles; $R_6$ is hydroxy or protected hydroxy; and Y, n and $R_1$ are as defined in formula (I), and thereafter deprotecting $R_6$ when protected hydroxy.

The reaction is suitably carried out in an inert solvent, such as hexamethylphosphoramide or N,N-dimethylformamide, as room temperature, in the presence of a base such as lithium carbonate.

Protected $R_6$ hydroxy groups may be converted to hydroxy $R_6$ groups by for example, de-acylation or de-alkylation reactions.

Suitable examples of D include activated ester moieties such as tosylate and mesylate and halogens such as bromide and iodide, preferably mesylate or bromide.

Suitable protected hydroxy groups $R_6$ are as hereinbefore described for protected hydroxy groups $R_3$.

Process Variant (b)

The invention also provides a further process for the preparation of a compound of the formula (I) which process comprises reacting a compound of formula (XII):

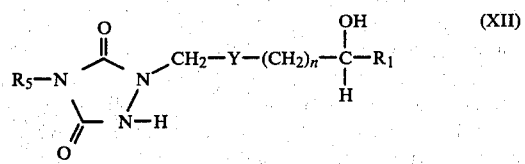
(XII)

wherein: Y is $CH_2$—$CH_2$— or —CH=CH—; and n, $R_1$ and $R_5$ are as defined in formula (I), with a compound of formula (XIII):

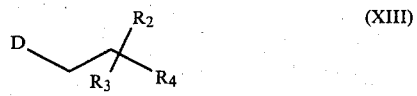
(XIII)

wherein D is a group readily displaced by nucleophiles, and $R_2$, $R_3$ and $R_4$ are as defined in formula (I).

This reaction is suitable carried out in an inert organic solvent, such as hexamethylphosphoramide or N,N-dimethylformamide, at room temperature, in the presence of a base, such as sodium carbonate or sodium hydride, and a source of halide ions, such as an alkali metal halide. Suitable alkali halides include sodium iodide and lithium iodide.

Suitable examples of D include those hereinbefore described for compounds of formula (XI). Preferably D is a tosylate residue.

Process Variant (c)

The present invention also provides another process for the preparation of a compound of the formula (I) which process comprises reacting a compound of the formula (XIV)

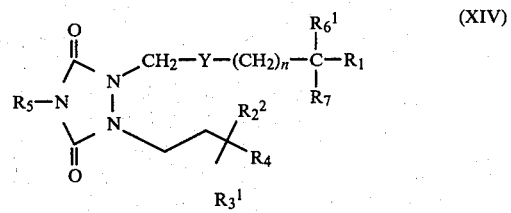
(XIV)

wherein $R_2{}^2$ and $R^1_3$ are as defined for $R_2$ and $R_3$ in formula (I) or $R^2_2$ and $R^1_3$ together form an oxo group; $R^1_6$ is hydroxy or protected hydroxy; $R_7$ is hydrogen or $R^1_6$ and $R_7$ together form an oxo group and at least one of $R^2_2+R^1_3$ and $R^1_6+R_7$ are oxo with either (i) a carbonyl reducing agent or (when $R^1_6$ is hydroxy or protected hydroxy) (ii) an alkyl or phenyl Grignard reagent (or similar metallic complex) and thereafter deprotecting $R^1_6$ when protected hydroxy.

The necessary reaction of a compound of the formula (XIV) may be carried out with any of the usual carbonyl-usual carbonyl-reducing agents or Grignard reagents under conditions which will be readily apparent to the skilled man.

Suitably borohydrides, such as sodium or lithium borohydrides in a solvent such as diglyme, an alcohol or an ether, or $BH_3$ in tetrahydroguran may be used in the reduction step.

Protected $R^1_6$ hydroxy groups may be deprotected as described under process variant (a).

The preparation of intermediates of the formulae (X), (XII) and (XIV) may be prepared by methods described in published European Patent Application No. 79301142.0 or by analogous methods thereto.

The groups $R_3$ and Y in the compounds of formula (I) may be varied by any conventional reactions. Thus for example protected hydroxy $R_3$ groups may be converted to hydroxy $R_3$ groups by de-acylation or de-alkylation.

Similarly, compounds of the formula (I) wherein Y is a —C≡C— or —CH=CH— group may be converted to their corresponding —CH=CH— or —CH$_2$—CH$_2$— analogues by any of the usual reduction methods, for alkenes and alkynes such as palladium catalysed hydrogenation.

It will of course be realised that the compounds of the formula (I) have asymmetric centres, and thus are capable of existing in enantiomeric and diasteriomeric forms. The invention extends to each of these isomeric forms, and to mixtures thereof.

It will be realised that when Y is CH=CH, this group may exist in the E and Z conformations. The invention extends to compounds of the formula (I) containing Y in each of these isomeric forms.

The different isomeric forms may be resolved or separated as appropriate by the usual methods.

Compounds of the formula (I) have useful pharmacological activity. For example compounds of the formula (I) have anti-gastric secretion activity; anti-ulcer activity; activity on smooth muscle, such as vascular activity, e.g. anti-hypertensive activity, effects on the respiratory tract, e.g. bronchodilation activity, anti-fertility activity and gastrointestinal smooth muscle activity; platelet aggregation inhibition acitivity and/or cardiac activity, e.g. anti-arrhythmic acitivity and/or anti-hypertensive activity.

Compounds of the formula (I) may accordingly be used in the treatment of the corresponding disorders in humans and animals.

The compounds of the formula (I) are especially useful bronchodilation agents.

In general it may be said that compounds of the formula (I) have a range of pharmacological activities similar to those shown by the natural prostaglandins, but that their activity profiles tend to be rather more selective, so that each compound tends to have a major activity readily ascertained by routine pharmacological tests.

The invention therefore also provides a pharmaceutical composition comprising a compound of the formula (I) and a pharmaceutically acceptable carrier.

In order to utilise the selectivity of activity found with compounds of the formula (I), normally a given compound will be used in the treatment of the disorder corresponding to the compound's major activity (that is, the disorder for which the compound has the lowest active dose) and will accordingly be formulated into the corresponding pharmaceutical composition, and administered in a manner conventional for treatment of that disorder. It may also of course be possible with compounds having one or more further pronounced activities to formulate and use the compound for those further activities as well as for the major activity, provided that there is no undesirable pharmacological interaction between the different activities, or that separation of the different activities can be obtained by a difference in the formulation or in the mode of administration.

The compositions may be in the form of tablets, capsules, powders, granules, lozenges or liquid preparations, such as oral or sterile parenteral solutions or suspensions.

Tablets and capsules for oral administration may contain conventional excipients such as binding agents, fillers, tabletting lubricants, disintegrants and acceptable wetting agents and the like. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms may be prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings or domestic animals which comprises the administration to the sufferer of an effective amount of a compound of the formula (I).

The following Example illustrates the preparation of the active compounds of the invention.

EXAMPLE 1

1-(9'-Hydroxydecyl)-2-(3''-hydroxy-3'',4''-dimethyloctyl)-4-methyl-1,2,4-triazolidine-3,5-dione (Compound 1)

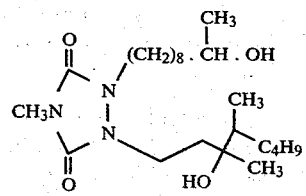

1-(9'-Oxodecyl)-2-(3''-hydroxy-3'',4''-dimethyloctyl)-4-methyl-1,2,4-triazolidine-3,5-dione (375 mg; 0.88 mmol) in dry ethanol (15 ml) was stirred at room temperature and sodium borohydride (50 mg) added portionwise over 2 hr. After stirring for a further 30 min., the excess of borohydride was decomposed with glacial acetic acid and the mixture evaporated in vacuo. The residue was partitioned between water (50 ml) and ether (50 ml), and the organic layer washed with water (1×50 ml), brine (1×50 ml), dried ($Na_2SO_4$) and evaporated in vacuo gave 1-(9'-hydroxydecyl)-2-(3''-hydroxy-3'',4''- dimethyl octyl)-4-methyl-1,2,4-triazolidine-3,5-dione as a colourless gum (368 mg; 97%).

Compounds 2 to 8 shown in Table 1 were prepared in a similar manner.

TABLE 1

$$\text{CH}_3\text{—N} \underset{\underset{\text{O}}{\|}}{\overset{\overset{\text{O}}{\|}}{\underset{\text{N}}{\overset{\text{N}}{\bigg\langle}}}} \begin{array}{l} \text{CH}_2\text{—Y—(CH}_2)_n\text{—}\overset{\text{OH}}{\underset{\text{H}}{\overset{|}{\text{C}}}}\text{—CH}_3 \\ \phantom{\text{N}}\underset{\text{OH}}{\overset{\phantom{|}}{\underset{\phantom{|}}{\text{R}_2}}} \\ \end{array}$$

| Compound | n | Y | $R_2$ | $R_4$ |
|---|---|---|---|---|
| 1 | 5 | —CH$_2$—CH$_2$— | CH$_3$ | CH(CH$_3$)C$_4$H$_9$ |
| 2 | 4 | —CH$_2$—CH$_2$— | H | C$_5$H$_{11}$ |
| 3 | 4 | —CH≐CH— | CH$_3$ | CH(CH$_3$)C$_4$H$_9$ |
| 4 | 4 | —CH$_2$—CH$_2$— | CH$_3$ | C$_6$H$_{13}$ |
| 5 | 3 | —CH$_2$—CH$_2$— | CH$_3$ | C$_6$H$_{13}$ |
| 6 | 5 | —CH≡CH— | CH$_3$ | CH(CH$_3$)C$_4$H$_9$ |
| 7 | 4 | —CH≐CH— | CH$_3$ | —C$_6$H$_{11}$ (cyclohexyl) |
| 8 | 4 | —C≡C— | CH$_3$ | —C$_6$H$_4$—F |

Analytical Data

Compound 1

I.R. (cm$^{-1}$): 3450 (O-H); 1765 and 1690 (N—C=O).
N.M.R. (CDCl$_3$)τ: 6.00–6.65 (7H, m, 2×N-C$\underline{H}_2$+2×OH+C$\underline{H}$-O protons); 6.95 (3H, s, N-C$\underline{H}_3$); 8.10–9.20 (32H, m, C$_8$H$_{15}$+—(CH$_2$)$_7$—chains+C-$\underline{H}_3$—); 8.88 (3H, s, C$\underline{H}_3$-tertiary alcohol).

Compound 2

I.R. (cm$^{-1}$): 3450 (O-H); 1765 and 1690 (N-C=O).
N.M.R. (CDCl$_3$)τ: 5.62 (2H, s, ex D$_2$O, 2×OH); 6.00–6.70 (6H, m, 2×N-C$\underline{H}_2$ and 2×C$\underline{H}$-O protons); 6.95 (3H, s, N-CH$_3$); 8.20–9.00 (22H, m, —(CH$_2$)$_6$— and —(CH$_2$)$_5$— chains); 8.84 (3H, d, J 6 Hz, C$\underline{H}_3$.CH.O); 9.12 (3H, m, terminal CH$_3$—).

Compound 3

I.R. (cm$^{-1}$): 3450 (O-H); 1765 and 1700 (N—C=O). 1590 (C=C).
N.M.R. (CDCl$_3$)τ: 4.12–4.80 (2H, d, N-C$\underline{H}_2$.C=C); 6.00–6.50 (5H, m, N-C$\underline{H}_2$+CH.OH+OH); 6.94 (3H, s, N-C$\underline{H}_3$); 7.65–8.00 (2H, m, C=C.C$\underline{H}_2$);

Compound 4

I.R. (c.m.$^{-1}$): 3450 (OH), 1690 and 1760 (N-C=O).
N.M.R. (CDCl$_3$)τ: 6.0–6.6 (5H, m, 2×NCH$_2$, OH); 6.95 (3H, s, NCH$_3$); 8.0–8.9 (30H, m, C$_8$H$_{15}$+(CH$_2$)$_6$ chain+CH$_3$) 9.1 (3H, brt, (CH$_2$)$_5$C$\underline{H}_3$).

Mass Spectrum: m/e (M*) C$_{22}$H$_{43}$N$_3$O$_4$ requires 413.3254, found 413.3240.

Compound 5

I.R. (cm$^{-1}$): 3450 (OH), 1770 and 1690 (N-C=O).
N.M.R. (CDCl$_3$)τ: 6.0–6.6 (5H, m, 2×NCH$_2$+C$\underline{H}$-O) 6.93 (3H, s, N-CH$_3$) 7.85 (2H, s, 2×OH) 8.10–9.15 (31H, m, C$\underline{H}_3$-CHO, (CH$_2$)$_5$ and C$_9$H$_{18}$ chains).

Mass Spectrum: m/e (M*) C$_{21}$H$_{41}$N$_3$O$_4$ requires 399.3097, found 399.3086.

Compound 6

N.M.R. (CDCl$_3$)τ: 5.73 (2H, t, N.CH$_2$.C≡C); 6.00–6.60 (3H, m, N.CH$_2$+CHOH); 6.95 (3H, s, N-CH$_3$); 7.20 (2H, s, ex D$_2$O; 2×OH); 7.60–9.30 (31H, m, C$_9$H$_{18}$ and C$_6$H$_{13}$ chains).

Mass spectrum: m/e (M*) C$_{23}$H$_{41}$N$_3$O$_4$ requires 423.3097, found 423.3102.

Compound 7

I.R. (cm$^{-1}$): 3430 (O-H); 2920 and 2840 (C-H); 1760 and 1680 (N-C=O).
N.M.R. (CDCl$_3$)τ: 4.10–4.90 (2H, m, olefinic protons); 5.60–6.65 (5H, m, 2×N.CH$_2$ and C$\underline{H}$,OH protons); 6.95 (3H, s, N-CH$_3$); 7.10 (2H, s, ex D$_2$O, 2×OH) 7.60–9.30 (21H, m, —(CH$_2$)$_4$-chain, +CH$_2$+cyclohexyl); 8.81 (3H, d, J7.5 Hz, C$\underline{H}_3$.CH.OH); 8.90 (3H, s, tertiary CH$_3$).

Mass spectrum: m/e (M*) C$_{22}$H$_{39}$N$_3$O$_4$ requires 409.2939, found 409.2925.

Compound 8

I.R. (c.m.$^{-1}$): 3450 (O-H); 2940 (C-H); 2220 (C≡C—) 1770 and 1695 (N-C=O); 1600 (aromatic C=C).
N.M.R. (CDCl$_3$)τ: 2.45–3.20 (4H, m, aromatic protons); 5.90 (2H, t, N.CH$_2$.C≡C); 6.20–6.70 (3H, m, N-CH$_2$ and C$\underline{H}$.OH protons); 7.05 (3H, s, N-CH$_3$); 7.65–8.20 (4H, m, 2×CH$_2$); 8.53 (3H, s, tertiary CH$_3$); 8.50–8.80 (6H, m, —(CH$_2$)$_3$-chain); 8.90(3H, d, J7.5 Hz, C$\underline{H}_3$.CH.OH)

Mass Spectrum: m/e (M*) C$_{22}$H$_{30}$N$_3$O$_4$F requires 419.2217, found 419.2227.

Pharmacological Data Section

Bronchdilation Activity

The compounds were examined for their ability to inhibit 5-hydroxytryptamine or histamine induced bronchoconstriction in the anaesthetised artificially respired guinear-pig (Konzett-Rossler preparation).

| Compound | ED$_{50}$ (µg per kg i.v.) |
|---|---|
| 1 | 20.0 |
| 3 | 17.5 |
| 4 | 4.2 |
| 7 | 160 |

Toxicity

No toxic effects were observed in this test.

We claim:

1. A compound of the formula:

$$\text{R}_5\text{—N} \underset{\underset{\text{O}}{\|}}{\overset{\overset{\text{O}}{\|}}{\underset{\text{N}}{\overset{\text{N}}{\bigg\langle}}}} \begin{array}{l} \text{CH}_2\text{—Y—(CH}_2)_n\text{—}\overset{\text{OH}}{\underset{\text{H}}{\overset{|}{\text{C}}}}\text{—R}_1 \\ \phantom{\text{N}}\underset{\text{R}_3\phantom{xx}\text{R}_4}{\overset{\phantom{|}}{\underset{\phantom{|}}{\text{R}_2}}} \\ \end{array}$$

wherein n has a value of from 3 to 5;

Y is —CH$_2$CH$_2$—, —CH=CH—; or —C≡C—;

R$_1$ is alkyl of 1 to 4 carbon atoms;

R$_2$ is hydrogen, alkyl of 1 to 4 carbon atoms or phenyl;

R$_3$ is hydroxy, acyloxy of 1 to 4 carbon atoms, methoxy or benzyloxy;

$R_4$ is hydrogen, alkyl of 1 to 9 carbon atoms, cycloalkyl of 3 to 8 carbon atoms, phenyl or naphthyl, said phenyl and naphthyl being unsubstituted or substituted with halo, trifluoromethyl, alkyl of 1 to 6 carbon atoms, hydroxy, alkoxy of 1 to 6 carbon atoms, phenyl(alkoxy of 1 to 6 carbon atoms in the alkoxy moiety or nitro; and $R_5$ is alkyl of 1 to 5 carbon atoms.

2. A compound according to claim 1 wherein
$R_2$ is hydrogen, methyl, ethyl or phenyl;
$R_3$ is hydroxy;
$R_4$ is hydrogen or alkyl of 1 to 9 carbon atoms.

3. A compound according to claim 2 wherein
n is 4 or 5;
$R_2$ is hydrogen, methyl or ethyl;
$R_4$ is alkyl of 4 to 9 carbon atoms;
$R_5$ is methyl; and
Y is —$CH_2CH_2$—.

4. 1-(8'-Hydroxy-n-nonyl)-2-(3''-hydroxy-3''-methyl-n-nonyl)-4-methyl-1,2,4-triazolidine-3,5-dione.

5. A compound according to claim 2 wherein
n is 4 or 5;
$R_2$ is hydrogen, methyl or ethyl;
$R_4$ is alkyl of 4 to 9 carbon atoms;
$R_5$ is methyl; and
Y is —CH=CH—.

6. 1-(cis-8''-Hydroxy-non-2-enyl)-2-(3''-hydroxy-3'',4''-dimethyloctyl)-4-methyl-1,2,4-triazolidine-3,5-dione.

7. A compound according to claim 1 wherein
$R_2$ is hydrogen, methyl, ethyl or phenyl;
$R_3$ is hydroxy; and
$R_4$ is cycloalkyl of 5 to 8 carbon atoms.

8. A pharmaceutical composition comprising a quantity of a compound according to claim 1 sufficient to effect bronchodilation together with a pharmaceutically acceptable carrier.

9. The method of effecting bronchodilation in a human or other animal which comprises administering thereto an effective amount of a compound according to claim 1.

* * * * *